United States Patent [19]

Cozad et al.

[11] Patent Number: 5,201,734

[45] Date of Patent: * Apr. 13, 1993

[54] SPINAL LOCKING SLEEVE ASSEMBLY

[75] Inventors: Trent E. Cozad, Fort Wayne; Antony J. Lozier, Warsaw; Jerry L. Lower, Bourbon, all of Ind.

[73] Assignee: Zimmer, Inc., Warsaw, Ind.

[*] Notice: The portion of the term of this patent subsequent to May 26, 2009 has been disclaimed.

[21] Appl. No.: 700,224

[22] Filed: May 14, 1991

Related U.S. Application Data

[62] Division of Ser. No. 287,245, Dec. 21, 1988, Pat. No. 5,074,864.

[51] Int. Cl.⁵ .............................................. A61F 5/01
[52] U.S. Cl. .................................... 606/62; 606/61
[58] Field of Search ............... 606/60, 61, 62; 128/69; 403/371, 342, 290, 367, 368

[56] References Cited

U.S. PATENT DOCUMENTS

| | | | |
|---|---|---|---|
| 731,635 | 6/1903 | Vandergrift et al. | |
| 953,896 | 4/1910 | Clattenburg | |
| 1,085,461 | 1/1914 | Michaelis | |
| 1,448,953 | 3/1923 | Grescio | 403/371 |
| 2,238,870 | 4/1941 | Haynes | 606/59 |
| 3,239,930 | 3/1966 | Violleau | 29/516 |
| 3,806,265 | 4/1974 | Hattan | 403/46 |
| 3,809,074 | 5/1974 | De Moude | 128/92 ZW X |
| 4,114,241 | 9/1978 | Bisping | 248/68.1 X |
| 4,198,174 | 4/1980 | Borowiec et al. | 403/44 |
| 4,199,070 | 4/1980 | Magnussen, Jr. | 248/68.1 X |
| 4,202,644 | 5/1980 | Soussloff | 403/369 |
| 4,274,401 | 6/1981 | Miskew | 128/69 |
| 4,361,141 | 11/1982 | Tanner | 128/69 |
| 4,369,769 | 1/1983 | Edwards | 128/69 |
| 4,404,967 | 9/1983 | Bacal et al. | 128/69 |
| 4,409,968 | 10/1983 | Drummond | 128/69 |
| 4,411,259 | 10/1983 | Drummond | 128/69 |
| 4,433,676 | 2/1984 | Bobechko | 128/69 |
| 4,567,884 | 2/1986 | Edwards | 128/69 |
| 4,611,582 | 9/1986 | Duff | 128/69 |
| 4,629,178 | 5/1987 | Keene | 128/69 |
| 4,641,636 | 7/1987 | Cotrel | 128/69 |
| 4,719,905 | 1/1988 | Steffee | 128/69 |
| 4,773,402 | 9/1988 | Asher et al. | 128/69 |
| 4,815,453 | 3/1989 | Cotrel | 128/69 |
| 4,827,918 | 5/1989 | Olerud | 128/92 |
| 4,836,196 | 6/1989 | Park et al. | 128/92 |
| 4,854,304 | 8/1989 | Zielke | 128/69 |
| 5,007,909 | 4/1991 | Rogozinski | 606/61 |
| 5,010,879 | 4/1991 | Moriya et al. | 128/69 |

FOREIGN PATENT DOCUMENTS

| | | |
|---|---|---|
| 0242708 | 10/1987 | European Pat. Off. |
| 2151475 | 3/1973 | France |
| 2244446 | 9/1973 | France |
| 1334867 | 10/1973 | United Kingdom |
| 2208476A | 4/1989 | United Kingdom |

OTHER PUBLICATIONS

Zimmer, Inc. publication-"Edwards Spinal Fixation System," -1984 (Lit, No. 84–008-8504–0281).

(List continued on next page.)

Primary Examiner—V. Millin
Assistant Examiner—J. Doyle
Attorney, Agent, or Firm—Margaret L. Geringer

[57] ABSTRACT

The present invention relates to a locking sleeve assembly for use in a posterior spinal system including components designed to be affixed to the spinal column of a person to correct for various lateral and sagittal deformities. The locking sleeve assembly is for interconnecting an elongated rod with another structure. The locking sleeve assembly includes an elongated sleeve having a bore therethrough. The sleeve has a tapered first end and a second end having a lock member thereon. The sleeve includes at least one split extending into the sleeve. The bore is sized to slidably receive the rod. The tapered surface of the sleeve is insertable into a tapered passage of the other structure with the rod in the bore, to form an interference fit between the two tapered surfaces. The locking sleeve assemblies are used in conjunction with the spinal system which also includes a pair of smooth surfaced rods mounted in spaced relation to one another on the spinal column in conjunction with various fixation devices such as clamps with hook bodies, hooks, screws with hook bodies, and couplers. Each such fixation device utilizes locking sleeve assemblies at each connection point to secure the respective fixation device to the respective rod or rods. The coupler assemblies are provided to maintain the spacing of the rods. The method of performing surgery using the posterior spinal system is also disclosed.

25 Claims, 9 Drawing Sheets

OTHER PUBLICATIONS

Zimmer, Inc. publication–"Interspinous Segmental Spinal Instrumentation: Surgical Technique," by Drummond/Keene–1984, 1987 (Lit. No. 97-8504-102, Rev. 1).

Zimmer, Inc. publication–"Knodt Distraction-Fuson Instrumentation," 1980. (Zimmer Spinal Catalog pp. 56-59).

Zimmer, Inc. publication–"Luque Segmental Spinal Instrumentation Surgical Technique," 1980 (Lit. No. 2261).

Zimmer, Inc. publication–"Wisconsin Compression System," 1980 (Lit. No. B-2260).

"A Locking Hook Spinal Rod System for Stabilization of Fracture-Dislocations," Jacobs et al, Clinical Orthopaedics and Related Research, No. 189, Oct., 1984, pp. 168-177.

Fenner Manheim publication–"Trantorque Keyless Shaft Mounts," 1981.

Stuart Inc. publication–"Universal Instrumentation (CD) For Spinal Surgery," by Dr. Cotrel/Dr. Dubousset–1985.

Zimmer, Inc. publication–"Harrington Spinal System, Six-Ratchet Distraction Rods, Gaines Hook Distractor," 1987 (Lit. No. 97-2250-01).

"A Newly Designed Chiba Solid Rod System for Scoliosis Surgery," Nakata et al, p. 171. Abstract of paper delivered at Scoliosis Research Society, 23rd Annual Meeting, Sep. 29-Oct. 2, 1988.

"Anthropometric Studies of the Human Sacrum Relating to Dorsal Transsacral Implant Designs," Asher et al., Clinical Orthopaedics and Related Research, No. 203, Feb. 1986, pp. 58-62.

"Biomechanical Comparisons of Spinal Fracture Models of the Stabilizing Effects of Posterior Instrumentations," Ferguson, et al., Spine, vol. 13, No. 5, 1988, pp. 453-460.

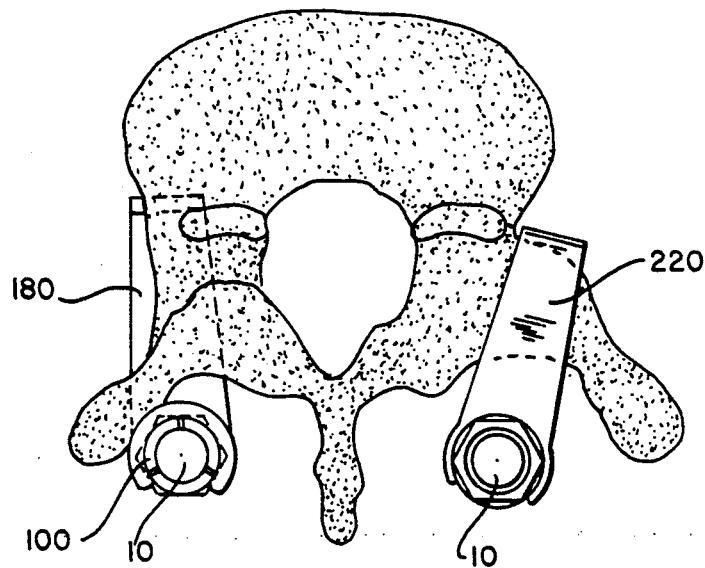
Fig. 8
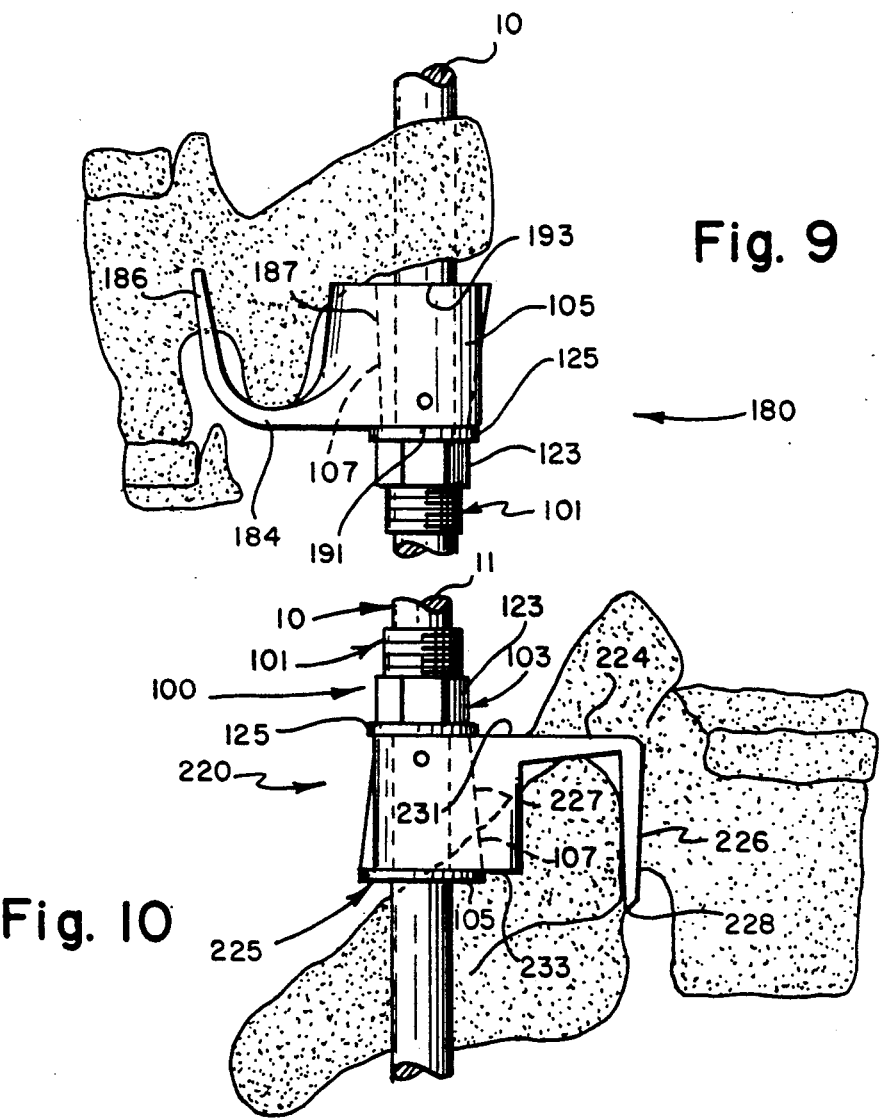
Fig. 9
Fig. 10

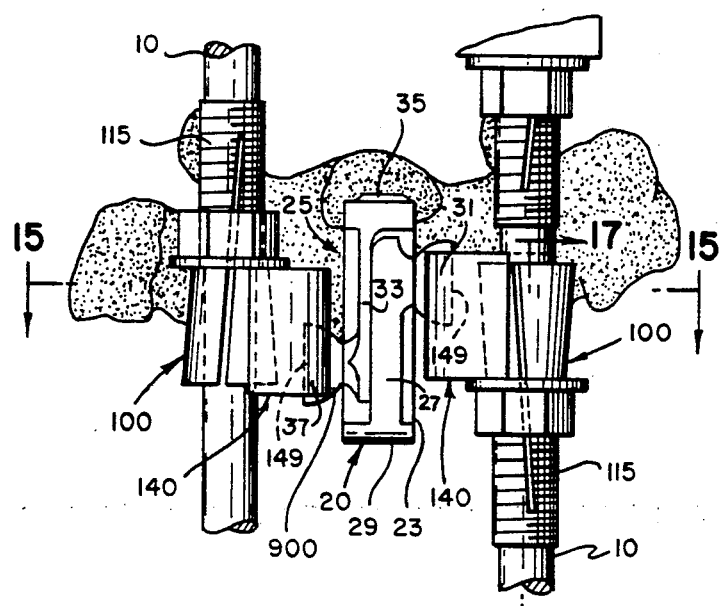
Fig.11
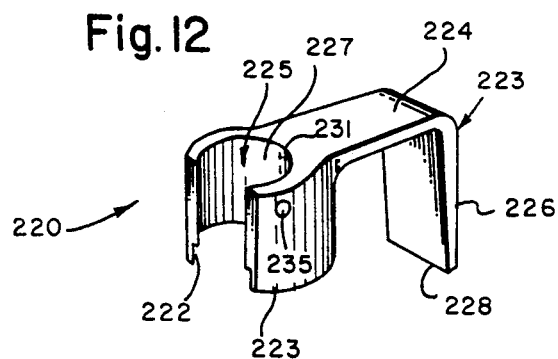
Fig.12
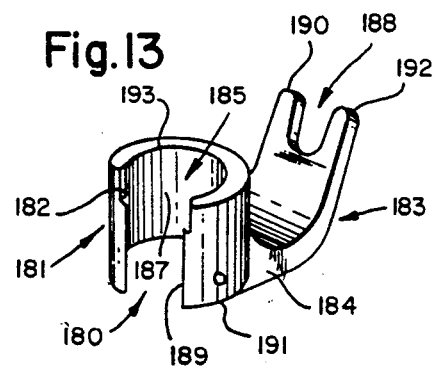
Fig.13
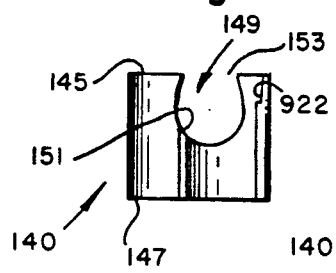
Fig.18
Fig.19
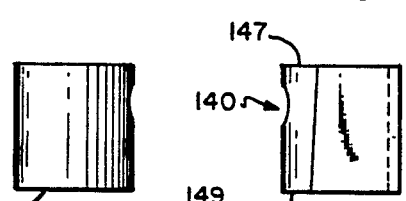
Fig.20 Fig.21
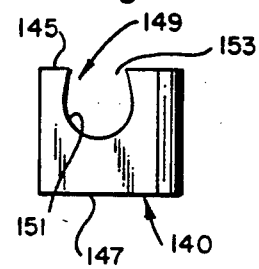
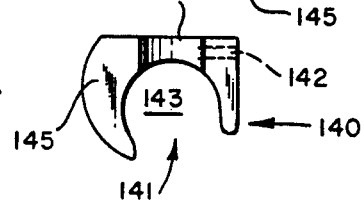
Fig.22

SPINAL LOCKING SLEEVE ASSEMBLY

This is a division of application Ser. No. 07/287,245 filed Dec. 21, 1988, now U.S. Pat. No. 5,074,864.

BACKGROUND OF THE INVENTION

The present invention relates to a posterior spinal system and method. In the prior art, posterior spinal systems are known. These systems include various appliances interconnected together to correct spinal column deformities.

In prior art systems, however, problems have developed, particularly as to the ability of the spinal rods to withstand the stresses placed thereon and as to the ability to mount various fixation appliances on the rods and maintain them in a desired position and orientation with respect thereto.

It has been found that modifications from a smooth surfaced rod, such as, for example, knurling or threading of the surface or providing ratchets along the rod, inherently result in weakening of the strength of the rod by creating stress risers for crack initiation on the outer surface of the rod. It is further noted, for example, that a knurled rod would need a larger diameter to provide comparable strength to a corresponding unknurled or smooth rod of smaller diameter.

Furthermore, it has been found that requiring a surgeon to pre-mount the various appliances on the rods, as may be required when threaded rods are used, is an inconvenient surgical technique, since if the surgeon miscalculates and needs to add or remove various appliances to or from the rods, complications in surgery result, since the surgeon must remove the rods from the patient after they have already been placed in situ for the purpose of unthreading or threading, appliances, therefrom or thereto.

As such, a need has developed for a posterior spinal system having rods of increased strength and having attachment means designed to be used to attach the various appliances on the rod without the need for pre-assembly prior to placement of the rod.

The following prior art is known to applicants:

U.S. Pat. No. 4,202,644 to Soussloff discloses a mounting device designed to be used to mount a machine element on a rotary shaft. The device used two interlocking split sleeves with the inner sleeve having a threaded end engaged by a threaded member coupled to the outer sleeve, with rotations of the threaded member causing movement of the sleeves with respect to one another which, due to their interface which includes conical surfaces, causes an increase in the diameter of the combined sleeves to cause a wedging of the shaft into an opening on the machine element. This is different from the teachings of the present invention wherein a locking sleeve assembly is provided which uses a single sleeve having a tapered outer surface and a threaded end and wherein a lock nut is threaded over the threaded end and has a flange to bear against a side surface of an element which is to be locked onto a smooth shaft inserted through the sleeve.

U.S. Pat. No. 4,629,178 to Keene discloses an open back hook assembly for engaging a spinal column which includes the provision of a threaded rod to which respective sleeves and nuts are threadably mounted. Hooks are affixed to the rod by sliding them over the sleeves and tightening the respective nuts. This is different from the teachings of the present invention wherein the rods themselves are smooth throughout their lengths and connection of hooks or other fixation structures thereto is accomplished by wedging action between the hooks or other components with corresponding locking sleeve assemblies to secure them to the respective rod. Connector assemblies may be utilized between the rods Thus, the present invention has advantageous aspects over and above the teachings of Keene by providing a smooth surfaced rod which is inherently stronger than a threaded rod, and by providing a locking sleeve assembly which allows easier placement and removal of hooks or other components therefrom.

U.S. Pat. No. 4,274,401 to Miskew discloses an apparatus for correcting spinal deformities and the method of using the apparatus. In each embodiment of Miskew, the rod which is employed has either a threaded surface or a surface including a plurality of adjustment stop surfaces (FIG. 25). This is different from the teachings of the present invention wherein rods with smooth surfaces are employed as well as other distinctions.

U.S. Pat. No. 4,361,141 to Tanner discloses a scoliosis transverse traction assembly which acts as a tensioning device to maintain two spaced rods in position with respect to each other. The tensioning device includes a transverse threaded rod with a basket hook at one end and a transverse hook toward the other end. The position of the transverse hook is adjustable along the transverse rod. This is different from the turn-buckle-type coupler of the present invention.

U.S. Pat. No. 4,567,884 to Edwards discloses a spinal hook designed to be used with a spinal correction system, which system includes both threaded rods and rods with projecting annular surfaces (ratchets) thereon. The hooks of Edwards may be modified for use with the present invention by incorporating an open back and further adapting the hook to accept the locking sleeve of the present invention. However, the present invention is distinct from the teachings of Edwards.

U.S. Pat. No. 4,611,582 to Duff discloses a vertebral clamp designed to be used between two adjacent vertebrae through attachment to the laminae thereof. The clamp includes two clamp members, one for each vertebra and a threaded coupling member designed to be used to adjust the distance between the clamps to achieve the desired spacial relationship. In contrast with this teaching, the present invention includes midline clamps which may be used to fix the position of elongated smooth surfaced rods on the posterior spine.

U.S. Pat. No. 4,641,636 to Cotrel discloses a device for supporting the rachis which includes the use of both closed and open back hooks supported on a rod having a knurled surface defined in this patent as having "a multitude of aspirates 21, obtained for example by milling or turning." A screw member 25 is utilized to secure the hooks to the knurled rod. This is different from the teachings of the present invention wherein smooth surfaced rods are employed as well as other distinctions.

French Patent No. 2,151,475 to Cotrel discloses a spinal appliance designed to be attached between two greatly spaced points on a spinal column as best seen in FIG. 7 through the use of end hooks. This is different from the teachings of the present invention wherein a desired curvature of the spine may be obtained by pre-bending a pair of smooth surfaced rods and affixing a plurality of components and appliances thereto to achieve a separation between the rods, as well as a desired configuration of the spine.

French Patent No. 2,244,446 to Cotrel discloses a transverse threaded rod to maintain two spaced spinal rods (one a ratcheted rod and one a threaded rod) in spaced relation with respect to each other. This is different from the turnbuckle-type coupler assembly of the present invention. Other distinctions also exist including, for example, the use in the present invention of smooth surfaced rods.

Zimmer Publication titled "Edwards Spinal Fixation System", 1984, discloses a spinal system developed in conjunction with Dr. Charles C. Edwards, including rods, sleeves and hooks. The sleeves (also described by U.S. Pat. No. 4,369,769 to Edwards) act as spacers between the spinal rod and the spine. The Edwards Anatomic Hooks shown in this publication correspond to the above-mentioned U.S. Pat. No. 4,567,884 to Edwards.

Zimmer Publication titled "Interspinous Segmental Spinal Instrumentation: Surgical Technique", by Dr. Denis S. Drummond and James Keene, 1984, discloses instruments and appliances used in performing spinal surgery. The system utilizes a paired, button/wire implant in which wires are tied to various types of spinal rods. The present invention does not utilize such a button/wiring technique.

Zimmer Publication titled "KNODT Distraction-Fusion Instrumentation", 1980, discloses the use of hooks mounted on threaded shafts designed to separate adjacent vertebrae from one another by a predetermined distance. This is different from the teachings of the present invention which uses open-backed hooks as well as smooth surfaced rods.

Zimmer Publication titled "Luque Segmental Spinal Instrumentation Surgical Technique", 1980, discloses segmental spinal instrumentation developed in conjunction with Dr. Edwardo R. Luque. In the Luque system and technique, elongated rods are used along with twisted wiring to hold the smooth rods in the desired spaced relation. This is different from the teachings of the present invention which does not utilize such a wiring technique.

Zimmer Publication titled "Wisconsin Compression System", discloses the use of prior art, Harrington, Keene and Drummond systems. The Keene hook disclosed in U.S. Pat. No. 4,269,178, discussed above, is employed and the use of threaded rods as well as rods having consecutive projections (ratchets) thereon is disclosed. The teachings of the present invention are distinct from the teachings of this publication, as including the use of rods which are smooth surfaced and wherein split sleeve locking assemblies are used to hold the various components on the rods.

An article entitled "A Locking Hook Spinal Rod System For Stablization of Fracture-Dislocations," Jacobs et al, *Clinical Orthopaedics and Related Research*, No. 189, October 1984, pp. 168-177, discloses a spinal system which utilizes a locking cover to secure the lamina in the hook and meshing radial grooves to lock the contoured rod to the upper and lower hooks. This is different from the smooth rod, open back hook and locking sleeves of the present invention.

SUMMARY OF THE INVENTION

The present invention relates to a locking sleeve assembly for use in a posterior spinal system and method. The locking sleeve assembly is for interconnecting an elongated rod with another structure. The locking sleeve assembly includes an elongated sleeve having a bore therethrough. The sleeve has a tapered first end and a second end having a lock nut thereon. The sleeve includes at least one split extending into the sleeve. The bore is sized to slidably receive the rod. The tapered surface of the sleeve is insertable into a tapered passage of the other structure with the rod in the bore, to form an interference fit between the two tapered surfaces. The sleeve assembly will be described in conjunction with the spinal system in order to provide an understanding of the clamp in conjunction with such a system. The inventive system includes the following aspects and features:

(a) In a first aspect of the present invention, the entire system revolves about the use of elongated rods with smooth surfaces throughout their respective lengths. Smooth, for the purposes of this application, is defined to be the absence of purposeful machining operations, such as threading, knurling, ratcheting or the like. However, smooth for the purposes of this application, could include polished surfaces as well as surfaces resulting from processes such as turning, grinding, forging and casting and could include light surface preparations such as dry blastings, shot peening or the like. As noted hereinabove, applicants have found that whenever the surface of an elongated rod is modified through knurling, threading, ratcheting or the like, the strength of the rod is weakened. As such, in order to maximize the strength of the inventive system, the rods used therein have smooth surfaces throughout their lengths.

(b) A plurality of different appliances and components are used in the inventive system and central to the inventive system is the manner of assembly of these various appliances and components to the above-described smooth surfaced rods. This manner involves the use of a locking sleeve assembly at each connection point of a respective appliance and/or component to a respective rod.

(c) Each locking sleeve assembly includes an elongated sleeve having one end which is tapered and another end which is threaded. A plurality of circumferentially-spaced angularly related splits are provided through the sleeve to allow the sleeve to be compressed. One of these splits extends the entire length of the sleeve. A lock nut may be threaded over the threaded end of the sleeve, which lock nut includes a radially outwardly extending flange. The sleeve has an opening therethrough designed to slidably receive a smooth surfaced rod. In the operation of the locking sleeve assembly, when it is desired to attach an appliance or component to a smooth surfaced rod, the sleeve is placed over the rod and the appliance or component is mounted on the sleeve over the tapered end thereof. As the lock nut is threaded over the threaded end of the sleeve, eventually, the flange thereof will engage a sidewall of the appliance or component to thereby cause the tapered end to be pulled through the opening in the appliance or component so that a wedging interaction therebetween is created to thereby cause the tapered end of the sleeve to frictionally engage the internal tapered walls of the opening in appliance or component while the splits in the sleeve allow the sleeve to be squeezed in frictional attachment over the rod.

(d) A further component forming a part of the inventive system consists of various styles of open back spinal hooks each hook having a shoe (or hook end portion) attached to a body having an open back allowing attachment over the tapered end of the sleeve of the locking sleeve assembly described hereinabove. The spinal hook may be attached on a respective smooth surfaced rod in the manner described in paragraph (c). Many styles of spinal hooks can be adapted or modified to incorporate the open back features for use with the locking sleeve assembly of the present invention. Examples of such hooks which can be adapted to incorporate such features are bifid hooks, Andre hooks, "lamina" or Edwards hooks as well as others.

(e) A further component forming an integral part of the inventive system is termed a "mid-line clamp assembly" and is designed to be centrally mounted in vertical orientation on the posterior spine. The mid-line clamp assembly, in the preferred embodiment thereof, may be made in two sizes, termed small and large. Each clamp assembly includes two shoes, each of which is mounted on a respective clamp half with the clamp halves being mounted together in a sliding interconnection. The respective clamp halves and shoes are termed "superior" and "inferior". In the small clamp assembly, the inferior clamp half has a single stud extending perpendicularly therefrom, as does the superior clamp half. In the large mid-line clamp assembly, each of the clamp halves is more elongated than is the case in the small mid-line clamp assembly, and in the large mid-line clamp assembly, the superior clamp half has two spaced such studs.

(f) The mid-line clamp assemblies are incorporated into the inventive system, in assembly, through the use of open-backed hook bodies. Each such hook body includes a circular recess designed to detachably receive a respective stud from a respective clamp half of a clamp assembly and further includes an open back allowing placement over the tapered end of a sleeve of a locking sleeve assembly. Once the lock nut of the locking sleeve assembly has been threaded to a position wherein the flange thereof engages a sidewall of the hook body to thereby pull the tapered end of the sleeve thereof through the open backed portion of the hook body to thereby lock the hook body in mounted position on a smooth surfaced rod, the above-described stud will also be locked in the circular recess against removal until such time as the hook body is removed from the locking sleeve assembly. The circular recess of the open backed hook body is sized to also receive the stud like head of a pedicle screw (not shown). Again, when the open backed hook body is mounted on the smooth surfaced rod by virtue of operation of a locking sleeve assembly, the pedicle screw may not be removed from the circular recess thereof.

(g) In the intended mode of use of the inventive system, a pair of smooth surfaced rods are mounted on the posterior spine through the use of the above-described appliances and components. In order to complete the assembly of the inventive system on the posterior spine, it is necessary to maintain the space of the two smooth surfaced rods from one another, thus increasing stability. For this purpose, coupler assemblies are provided each of which includes a pair of open backed bodies which may be moved toward and away from one another by virtue of a turnbuckle device. Each of the respective bodies may be mounted over a respective smooth surfaced rod through the use, in each case, of a locking sleeve assembly in the manner described in detail hereinabove. With such mounting having taken place, the turn buckle device may be rotated to adjust the spacing between the bodies of the coupler assembly.

In the practice of surgery, using the posterior spinal system of the present invention, the following steps may be undertaken:

(1) First, the site is prepared through performance of an incision followed by prepping of sites for hooks and mid-line clamps. Spinous process carpentry or controlled cutting of the bone is undertaken where required to prep the various portions of the spinal column for receipt of the clamps.

(2) The various hooks and clamps are placed in position at the prepped sites.

(3) The smooth surfaced rods are contoured using rod bending means to the normal contours of the spinal column for the particular individual on whom the surgery is being performed.

(4) Thereafter, locking sleeve assemblies are mounted on the rod and are placed at or adjacent the appropriate positions with respect to the positions of the hooks and clamps as placed in position.

(5) The hooks and/or clamps are mounted on the rods through the use of the locking sleeve assemblies and the coupler assemblies are mounted on the rod via locking sleeve assemblies to define the spacing between the rods.

(6) Thereafter, the site is closed through the use of standard surgical techniques.

(7) Of course, as should be understood by those skilled in the art, additional components may be used in conjunction with technique described above, such as, for example, pedicle screws. Of course, depending upon the particular situations involved, either large or small mid-line clamp assemblies, or both, may be employed.

The inventive posterior spinal system is designed for use in treating idiopathic scoliosis, thoracolumbar fractures and kyphosis. Lateral correction, de-rotation and establishment of sagittal plain contours may be accomplished via nodal approximation. Both distraction and compression may be simultaneously employed on the same rod.

Accordingly, it is a first object of the present invention to provide a posterior spinal system and method of use thereof.

It is a further object of the present invention to provide such a posterior spinal system which uses rods having smooth surfaces throughout to increase strength and flexibility thereof.

It is a yet further object of the present invention to provide such a posterior spinal system with locking sleeve assemblies designed to be used to removably attach all components and assemblies to the smooth surfaced rods thereof.

It is a yet further object of the present invention to provide such a posterior spinal system which may include hooks, clamps, screws and other methods of spinal attachment.

It is a yet further object of the present invention to provide a method of performing surgery using the posterior spinal system of the present invention.

These and other objects, aspects and features of the present invention will be better understood from the following detailed description of the preferred embodiments when read in conjunction with the appended drawing figures.

BRIEF DESCRIPTION OF THE DRAWINGS

As seen in FIGS. 1 and 7, a spinal column 1 includes cervical vertebrae 2, thoracic vertebrae 3, lumbar vertebrae 5 and the sacrum 7.

FIG. 1 shows a posterior view of a human spinal column with a first example of the inventive posterior spinal system affixed thereto.

FIG. 7 shows a posterior view of a human spinal column having a second example of the inventive posterior spinal system affixed thereto.

FIG. 8 shows a cross-sectional view along the line 8—8 of FIG. 7.

FIG. 9 shows a cross-sectional view along the line 9—9 FIG. 7.

FIG. 10 shows a cross-sectional view along the line 10—10 of FIG. 7.

FIG. 11 shows an enlarged view of a portion of FIG. 1.

FIG. 12 shows a perspective view of a lamina hook which forms a part of the inventive system.

FIG. 13 shows a perspective view of a bifid hook which forms a part of the inventive system.

FIGS. 18, 19, 20, 21 and 22 show views from various perspectives of a hook body which forms a part of the inventive system.

SPECIFIC DESCRIPTION OF THE PREFERRED EMBODIMENT

Figure 1:
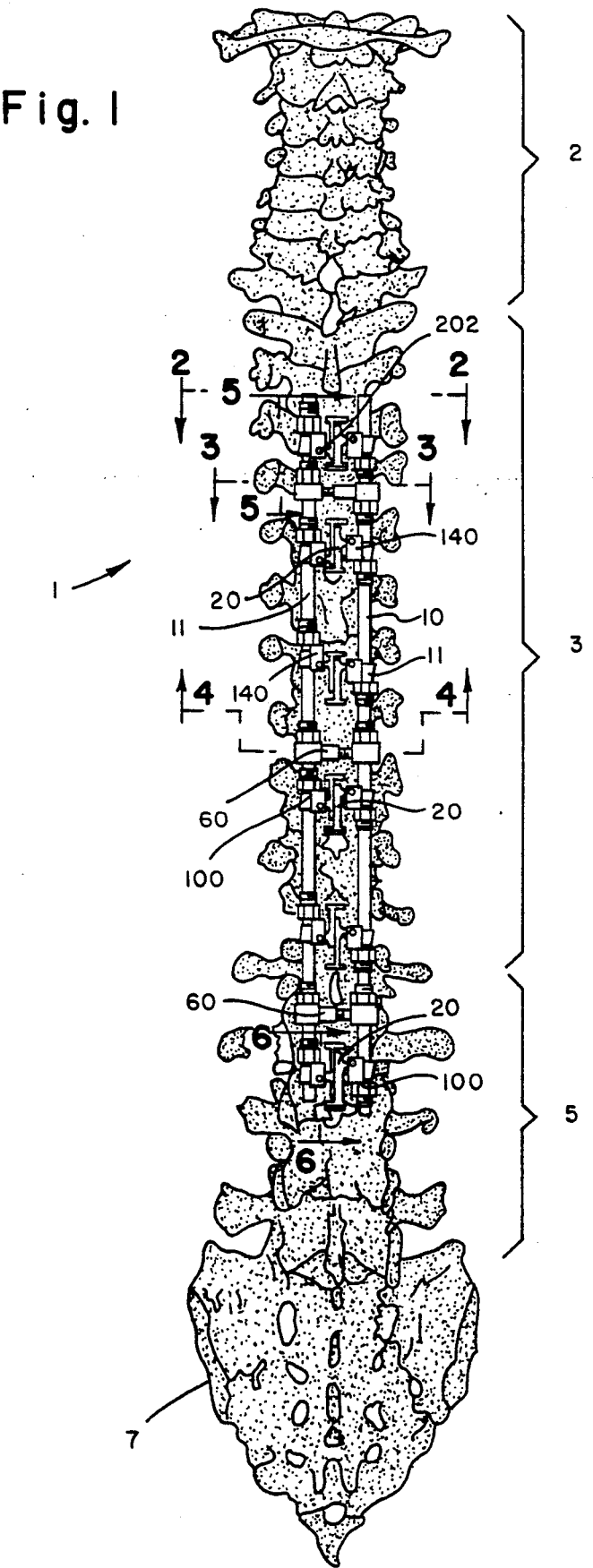
FIGS. 1 and 7 show two examples of a spinal column having examples of the inventive posterior spinal system mounted thereon.
Figure 2:
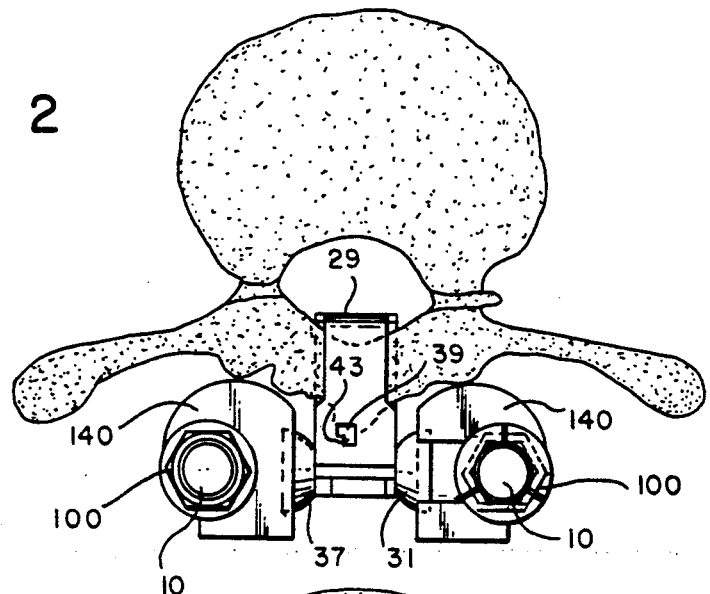
FIG. 2 shows a cross-sectional view along the line 2—2 of FIG. 1.
Figure 7:
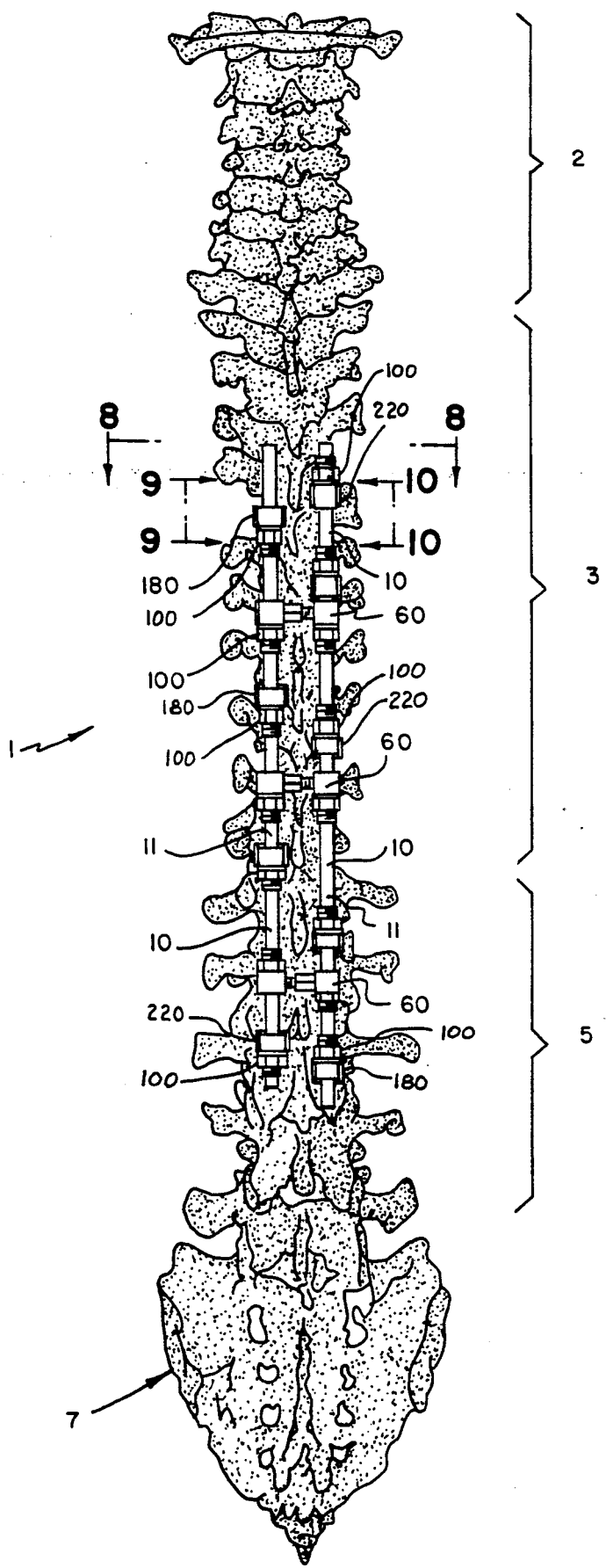

FIGS. 1 and 7 show two examples of the use of the inventive posterior spinal system.

FIG. 1 shows a pair of rods 10, each of which has a smooth surface 11 throughout its length. The rods 10 are affixed in spaced relation with respect to one another by virtue of a plurality of mid-line clamps 20 and coupler assemblies 60. The mid-line clamps 20 and coupler assemblies 60 are affixed to the rods 10 through the use of locking sleeve assemblies 100, with the mid-line clamps 20 utilizing hook bodies 140 interposed between the respective mid-line clamps 20 and locking sleeve assemblies 100.

In the example of FIG. 7, the rods 10 have smooth surfaces 11 throughout their lengths and are mounted on the spinal column in fixed relationship with respect to one another through the use of the coupler assemblies 60 as well as through the use of bifid hooks 180 and lamina hooks 220. The coupler assemblies 60 and hooks 180, 220 are coupled to the rods 10 through the use of locking sleeve assemblies 100.

Figure 16:
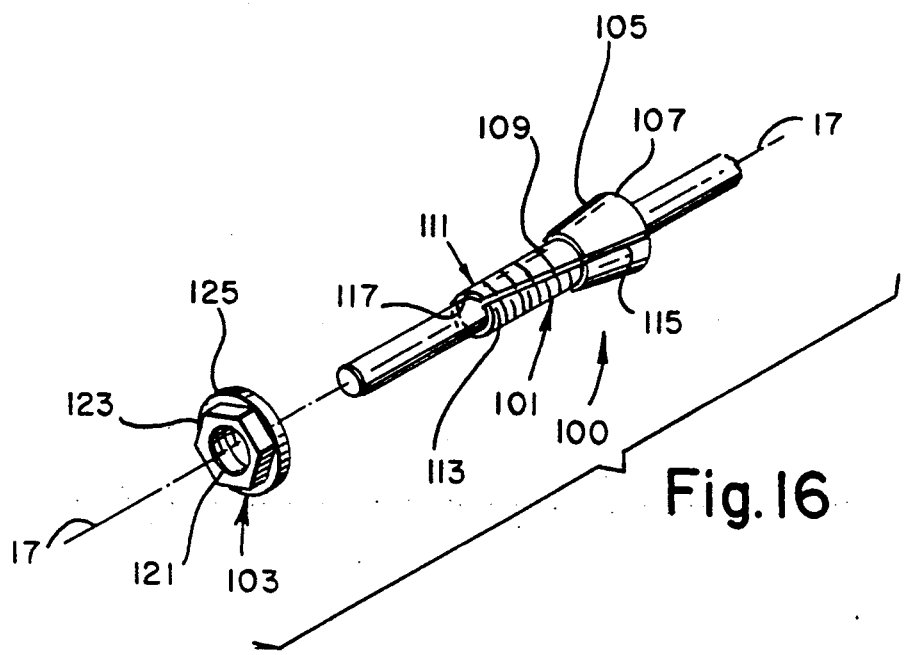
FIG. 16 shows an exploded perspective view of a locking sleeve assembly which forms a part of the inventive system.
Figure 17:
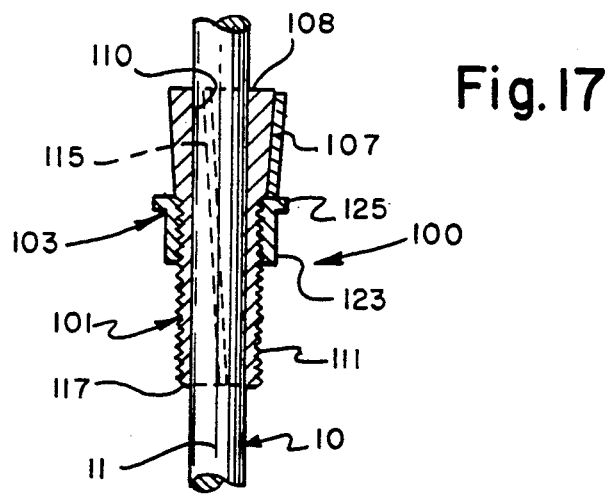
FIG. 17 shows a cross-sectional view along the line 17—17 of FIG. 11.

With reference, now, to FIGS. 16 and 17, a locking sleeve assembly 100 is seen to include an elongated sleeve 101 and lock nut 103. The sleeve 101 includes one end 105 having a surface 107 which tapers downwardly to a termination at a shoulder 109 from which extends another end 111 of the sleeve 101 which another end 111 includes screw threads 113 throughout its length.

A plurality of splits 115 are formed at an oblique angle to the longitudinal direction of elongation of the sleeve 101 with the splits 115 terminating just short of the end 117 of the sleeve 101. Such termination of the splits 115 maintains the structural integrity of the sleeve 101. However, one of these splits 115 may extend the entire length of the sleeve 101. It is advantageous for the slits to be angled obliquely to reduce the risk of having the land between two adjacent slits from being exposed at the opening of the open-back hook or hook body.

The lock nut 103 includes a threaded passageway 121 therethrough with its outer surface consisting of a preferably hexagonally-shaped outer surface 123 and a radially outwardly extending flange 125.

With reference back to FIG. 17, sleeve 101, it should be understood that the surface 107 has a slight frusto-conical taper which increases in diameter in a direction away from the threaded portion 111 thereof.

Figure 3:
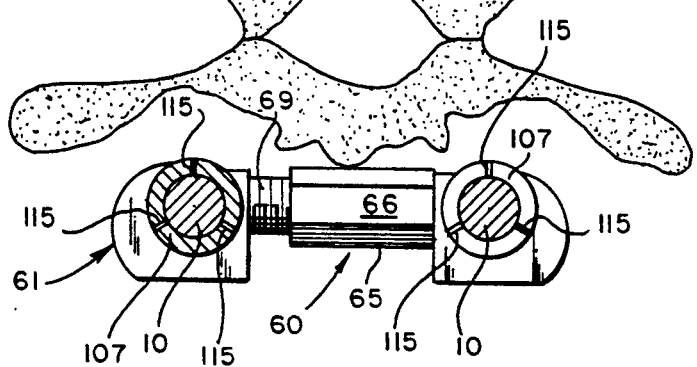
FIG. 3 shows a cross-sectional view along the line 3—3 of FIG. 1.
Figure 4:
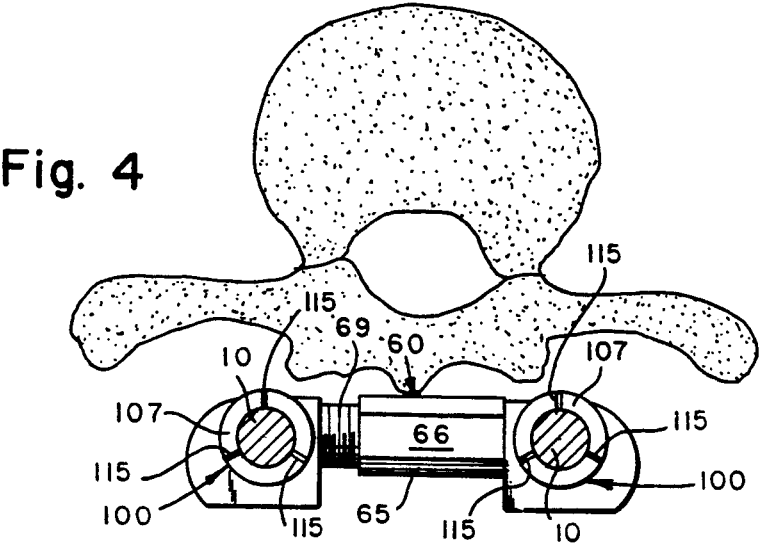
FIG. 4 shows a cross-sectional view along the line 4—4 of FIG. 1.

In the preferred embodiment of the present invention, the sleeve 101 includes three circumferentially-spaced splits 115, as illustrated, for example, in FIGS. 3 and 4.

As should be understood from the above description, the locking sleeve assembly 100 is advantageous in fixing the position of a component on a smooth surfaced rod 10. With reference to FIGS. 16 and 17, it should be understood that when a component is placed over the tapered surface 107, which component has a correspondingly tapered recess with an internal dimension smaller than the outer diameter of the surface 108 of the sleeve 101, when the locking nut 103 is threaded onto the threads 113 of the sleeve 101, and the flange 125 thereof bears against a sidewall of the component, such interaction causes interengagement of the tapered surface 107 of the sleeve 101 with tapered inner surfaces of the recess in the component (not shown in FIGS. 16 and 17) to thereby cause a wedging action which not only causes frictional retention of the surface 107 of the sleeve 101 on the inner surfaces of the recess of the component, but also causes compression of the sleeve 107, due to the existence of the splits 115 thereof to cause the inner surfaces 110 of the sleeve 101 to frictionally grip the smooth surface 11 of the rod 10 to thereby cause simultaneous retention of the locking sleeve assembly 100 in fixed relation on the rod 10 with a component mounted in fixed relation on the locking sleeve assembly 100. One example of a degree of taper which has been found appropriate for the surface 107 and the recess in the component is about 6 degrees from the longitudinal axis thereof. This interaction will be better understood from the description herein below of such figures as, for example, FIGS. 2, 4, 11, 12 and 13.

Figure 26:
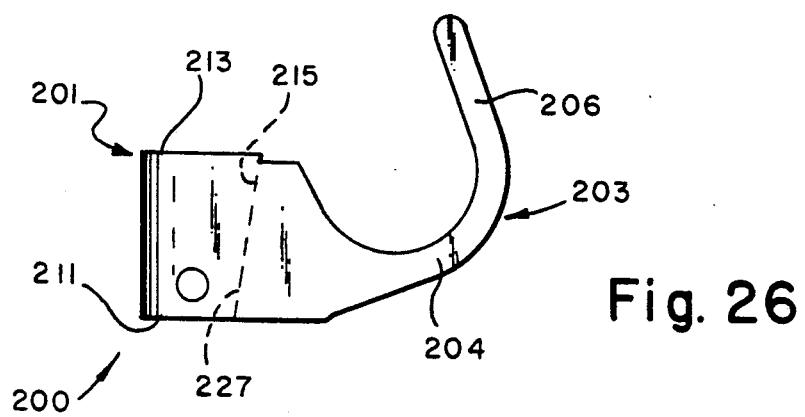
FIG. 26 shows a side view of an Andre hook which is included in the inventive system.

With reference, now, to FIGS. 12, 13 and 26, three examples of hooks which form a part of present invention are shown.

FIG. 12 shows a lamina hook 220 which includes a body 221 and a shoe 223 which forms a hook. The body 221 includes a recess 225 having an arcuate wall 227 with an opening 229, opening in a direction facing away from the shoe 223.

The arcuate wall 227 is tapered from a smaller diameter at the reference numeral 231 to a larger diameter adjacent the reference numeral 233. However, it is noted that a taper in the reverse direction (not shown) could also be utilized, if desirable. If desired, recesses 235 may be provided in the body 221 of the hook 220 to facilitate gripping of the hook 220 by a suitable instrument.

The shoe portion 223 of the lamina hook 220 includes a first leg 224 extending substantially perpendicularly to the direction of longitudinal elongation of the recess 225 of the body 221 of the hook 220, as well as a second leg 226 which is substantially perpendicular to the leg 224. The end 228 of the second leg 226 extends beyond the end 223 of the body 221, as best seen in FIG. 10. As further seen in FIG. 10, the lamina hook 220 is affixed to the rod 10 via a locking sleeve assembly 100. The tapered surface 107 of one end 105 of the sleeve 101 is seen in phantom in FIG. 10, as is the tapered surface 227 of the recess 225 of the hook 220. As should be understood from FIG. 10, when the flange 125 of the locking nut 103 engages the surface 231 of the hook 220, further rotation of the locking nut 103 with respect to the sleeve 101 will result in pulling of the end 105 of the sleeve 101 upwardly in view of FIG. 10 through the recess 225 in the body 221 of the hook 220 to thereby cause (1) wedging action between the surfaces 107 and 227, as well as (2) squeezing of the inner surfaces 110 of the sleeve 101 against the smooth surface 11 of the rod 10, to thereby rigidly affix the hook 220 thereon.

FIG. 13 shows a bifid hook 180 having a body 181 and a shoe portion 183 forming a hook. The body 181 includes a recess 185 having inner surfaces 187 the terminations of which define an opening 189. The surfaces 187 of the recess 185 taper from a smaller diameter at the end 191 to a wider diameter at the end 193. Again, it is noted that a taper in the reverse direction could also be utilized if desirable.

The shoe portion includes a first leg 184 and a second leg 186 attached thereto which leg 186 is bifurcated to form a recess 188 which separates two legs 190, 192.

As best seen in FIG. 9, the legs 184, 186 form a substantially continuous curve as opposed to the angular relationship between the legs 224 and 226 of the lamina hook 220, best seen in FIG. 10.

The manner of fixation of the bifid hook 180 to the rod 10 is analogous to the manner of fixation of the lamina hook 220 to the rod 10, as explained herein above with reference to FIGS. 10 and 12 in particular.

With reference to FIG. 26, a further hook termed an Andre hook is generally designated by the reference numeral 200 and is seen to include a body 201 and a shoe portion 203.

The body 201 includes a recess 205 seen in phantom, including recess walls 227 which taper from a smaller diameter adjacent the wall 211 to larger diameter adjacent the wall 213. An opening (not shown) in the recess 205 is analogous to the respective openings 229, 189 of the respective lamina hook 220 and bifid hook 180.

The shoe portion 203 includes a first leg 204 and a second leg 206 which are connected together in a continuous curve which differs from the shoe portion of the bifid hook 180, in that the terminus of the leg portion 206 faces toward the body 201 of hook 200, as seen in FIG. 26, as opposed to the configuration of the leg 186 of the bifid hook 180 which faces away from the body 181.

The manner of attachment of the Andre hook 200 to a smooth surfaced rod 10 is the same as the manner of installation of the respective bifid hook 180 and lamina hook 220.

In each hook, the open backed portion is widened at the widest end of the recess thereof to best facilitate the insertion of a sleeve 107 therein. This aspect is designated by the reference numerals 222 (FIG. 12) and 182 (FIG. 13).

Figure 14:
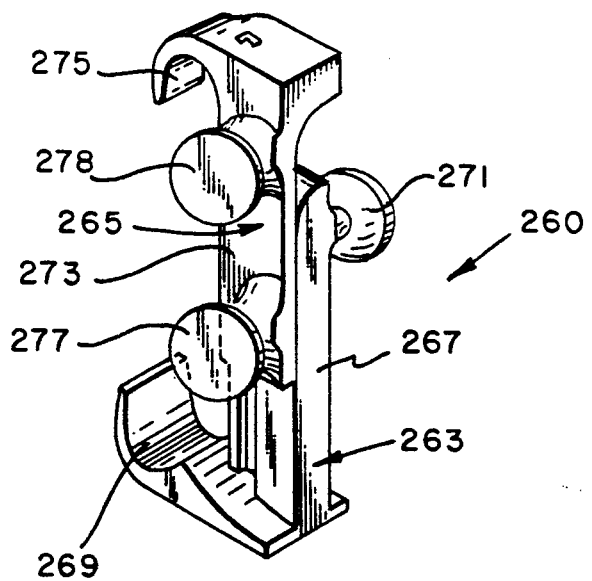
FIG. 14 shows a perspective view of a large mid-line clamp assembly which forms a part of the inventive system.
Figure 15:
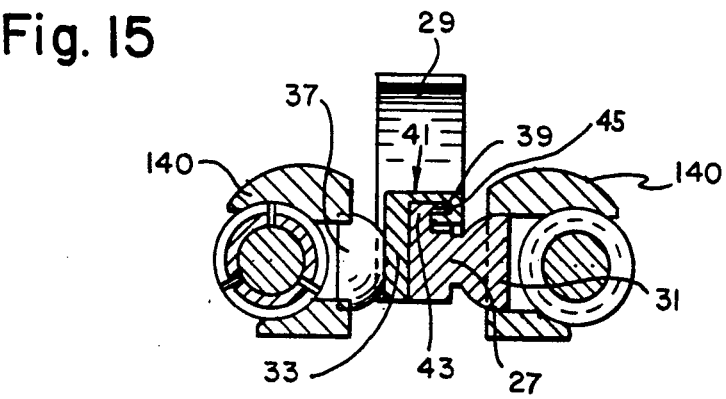
FIG. 15 shows a cross-sectional view along the line 15—15 of FIG. 11.

With reference, now, to FIGS. 11, 14 and 15, embodiments of a mid-line clamp assembly will be described in detail. With reference, first, to FIGS. 11 and 15, a small mid-line clamp assembly 20 is seen to include an inferior clamp half 23 and a superior clamp half 25. The inferior clamp half 23 includes a body 27 with a shoe 29 at one end thereof, and a transverse inferior stud 31 extending outwardly from an opposite end thereof.

The superior clamp half 25 includes a body 33 with a shoe 35 at one end, and a transverse superior stud 37 extending outwardly from an opposite end thereof. As should be understood from the analogous structure designated by the respective reference numerals 269 and 275, the shoes 29 and 35 are of hook-like configuration.

With particular reference to FIG. 15, it is seen that the body 33 of the superior clamp half 25 includes a recess 39 of L-shaped cross-section in which is slidably received a rib 41 of L-shaped cross-section having a neck portion 43 and a cross piece 45. The interaction between the recess and the rib allows easy sliding movement between the superior clamp half 25 and the inferior clamp half 23. It is understood that other slidable mating shapes could be utilized, such as a T-shaped cross-section, a dovetail-shaped cross-section, or any other suitable configuration.

With reference to FIG. 14, a large mid-line clamp assembly 260 is illustrated which is quite similar to the small mid line clamp assembly 20 best illustrated in FIGS. 11 and 15. The main difference between the large mid-line clamp assembly 260 and the small mid-line clamp assembly 20 lies in the fact that the clamp halves of the large mid-line clamp assembly 260 are elongated as compared to the respective lengths of the clamp halves of the small mid-line clamp assembly 20. Additionally, due to this elongation, the superior clamp half 265 of the large mid-line clamp assembly 260 has the provision of two spaced transversely extending studs 277 and 278.

With particular reference to FIG. 14, it is seen that the large mid-line clamp assembly 260 includes an inferior clamp half 263 and a superior clamp half 265. The inferior clamp half 263 includes a body 267 and a shoe 269 of hook-like configuration. As is seen in FIG. 14, the inferior shoe 269 is significantly wider than the superior shoe 275.

The superior clamp half 265 includes a body 273 and a shoe 275 of hook-like configuration. The clamp halves 263 and 265 are slidably connected to one another through the recess and L-shaped rib configuration best illustrated in FIG. 15 with regard to the small mid-line clamp assembly 20 and designated therein by the reference numerals 39, 41.

The inferior clamp half 263 has incorporated therewith a transverse outwardly extending stud 271 on an end of the body 267 thereof opposed to the end on which the shoe 269 is formed. The superior clamp half 265 includes two, spaced transversely extending studs 277 and 278 with the stud 278 lying adjacent the shoe 275 and with the stud 277 being located toward an end of the body 273 of the superior clamp half 265 opposed to the end on which the shoe 275 is formed. The inclusion of two studs, 277 and 278 on the superior clamp half 265 is provided to add versatility in the mounting of the large mid-line clamp assembly 260 on the posterior spine.

As is the case with the other components described herein above, the clamps 20 and 260 are removably attachable to respective smooth surfaced rods 10 through the use of locking sleeve assemblies. The studs are provided to facilitate this attachment of the clamp assemblies with respect to the smooth surfaces rods 10. Interposed between the respective studs and the respective rods are hook bodies 140, an example of which is illustrated in FIGS. 18–22.

With reference to FIGS. 18–22, the hook body 140 is seen to include an open back 141 leading to a recess 143 which is tapered from a larger diameter adjacent a wall 145 to a smaller diameter adjacent a wall 147. With particular reference to FIG. 22, an opening 142 is provided through a wall in the hook body 140 for the purpose of allowing the gripping of the hook body 140 by a suitable surgical instrument.

Intersecting the recess 143 and the wall 145 is a further recess 149 having curved walls 151 and an opening 153 at its junction with the wall 145. The recess 149 is sized and configured to receive one of the transverse studs of a mid-line clamp assembly. The recess 143 is sized and configured to be mountable over the tapered surface 107 of the end 105 of the sleeve 101 of a locking sleeve assembly 100.

A respective stud is inserted into a respective recess 149 through the opening 153 thereof, and after the hook body 140 has been securely mounted over a locking sleeve assembly 100, as should be understood from the above detailed description of such procedure, the said stud is captured in the recess 149 and may not be removed therefrom until the locking sleeve assembly 100 is subsequently loosened. This is the case because, with reference to FIG. 11, each stud has a narrowed neck 900 allowing the stud to be pushed inwardly in the recess 149 to allow removal of the stud therefrom. Intrusion of the end 105 of the sleeve 101 of the locking sleeve assembly 100 into the recess 143 of the hook body 140 prevents the inward movement of the stud which is necessary to allow its removal from the recess 149. Thus, this interaction of parts allows a secure assembly of a respective stud on a hook body 140.

As should be understood with reference to FIG. 11, two hook bodies 140 are used in conjunction with locking sleeve assemblies 100 and rods 10 to secure each mid-line clamp in assembled relation on the thoracic or lumbar lamina.

Figure 5:
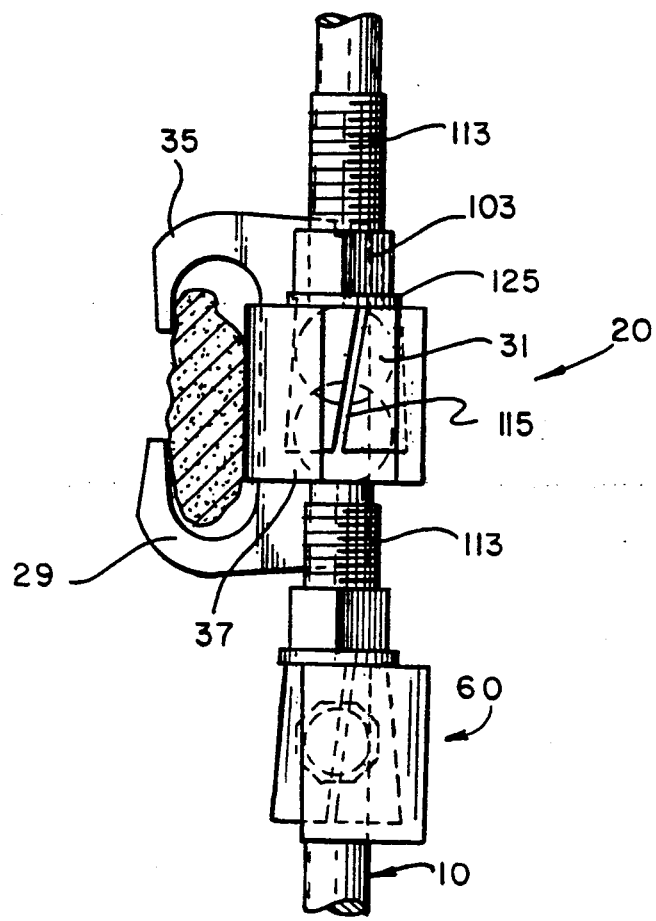
FIG. 5 shows a cross-sectional view along the line 5—5 of FIG. 1.
Figure 6:
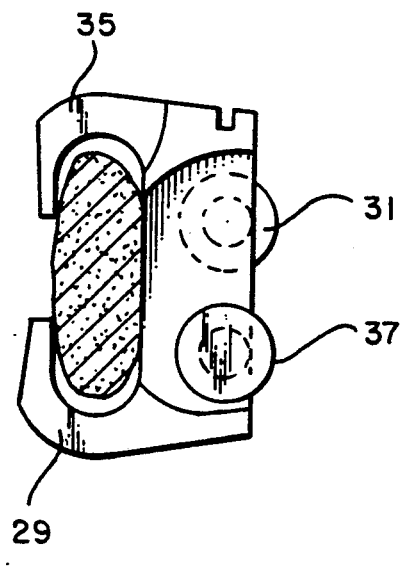
FIG. 6 shows a cross-sectional view along the line 6—6 of FIG. 1.

As seen with reference to FIGS. 5, 6 and 11, the hook bodies 140 are oriented in opposed directions on the respective smooth surfaced rods 10 and are attached thereto by virtue of locking sleeve assemblies 100 also mounted in opposed directions in a manner such that the studs 31 and 37 are captured by the respective recesses 149 in a manner opposing movement of the shoes 29, 35 away from one another. Thus, the clamp assembly 20 is initially placed over the mid-line of a thoracic or lumbar lamina and the bodies 27, 33 are slid with respect to one another to cause the shoes 29 and 35 thereof to grip both surfaces of the lamina. With the clamp assembly 20 held in such position, hook bodies 140 are attached over the respective studs 31 and 37 and are fastened in place through the use of locking sleeve assemblies 100 to maintain fixation of the mid-line clamp assembly 20 over the lamina and with respect to the two smooth surfaced rods 10.

The same procedure would be followed in placing and securing a large mid-line clamp assembly 260 over the lamina of a thoracic or lumbar vertebra and for the fixation thereof with respect to two smooth surfaced rods 10.

As has been explained hereinabove, it is desirable to provide some means for maintaining the spacing between two smooth surfaced rods 10 from one another to increase the stability of the system. For this purpose, coupler assemblies 60 are provided, as seen in FIGS. 1 and 7, to maintain the desired separation between the rods 10. An example of a such coupler assembly is seen in FIGS. 3, 4, 23, 24 and 25.

Figure 23:
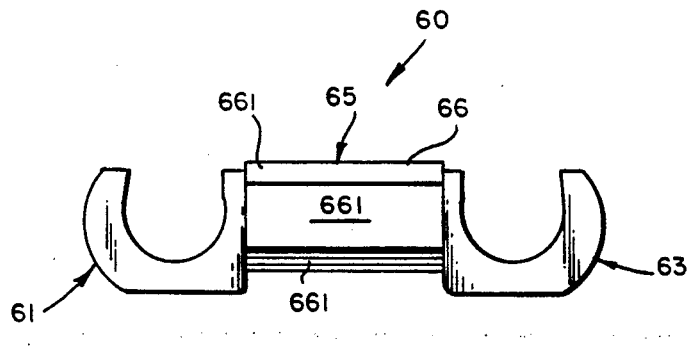
FIG. 23 shows a side view of a coupler assembly which forms a part of the inventive system.
Figure 25:
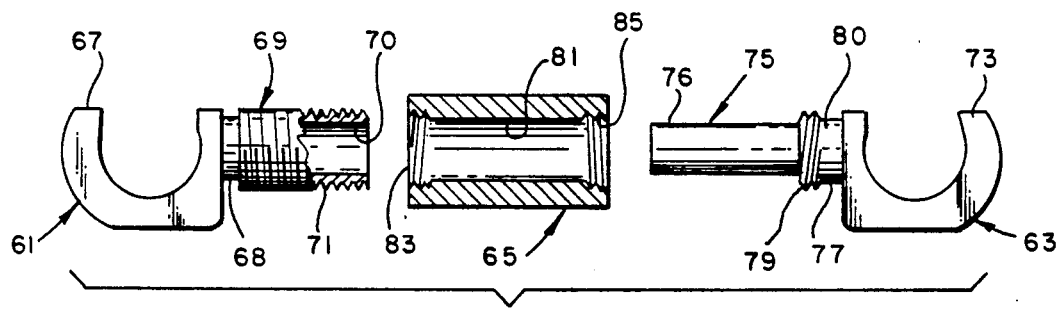
FIG. 25 shows a cross-sectional view from the side, of the inventive coupler assembly.
Figure 24:
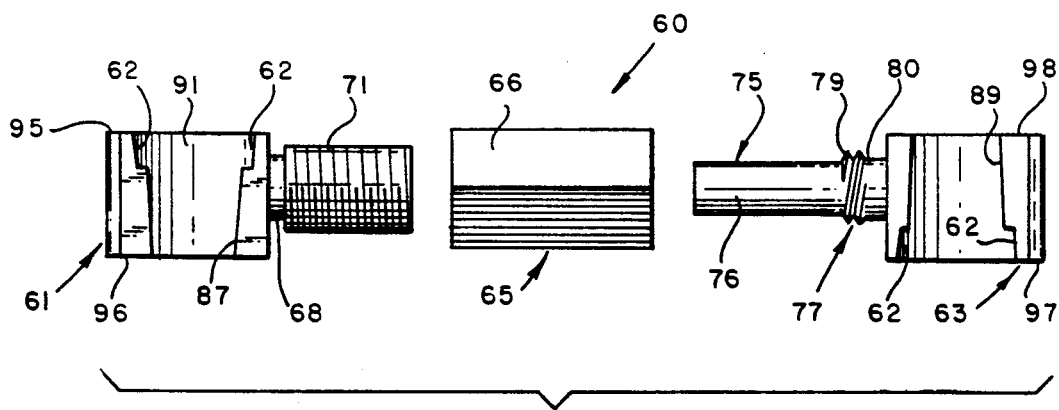
FIG. 24 shows an exploded bottom view of the coupler assembly.

With reference to FIGS. 23–25, the coupler assembly 60 is seen to include a first body 61, a second body 63 and a sleeve 65.

The body 61 includes an open backed retainer or head 67 and a rod or shaft 69 having right-hand threads 71 thereon. A short, narrowed neck 68 interconnects the rod 69 and the retainer 67.

With further reference to FIGS. 24 and 25 in particular, the body 63 includes an open backed retainer 73, a rod 75 having a smooth outer surface 76 and a neck 77 having left-hand threads 79 thereon. The rod 69 of the body 61 includes a central blind bore 70 therein which is sized to slidably receive therein the rod 75 of the body 63.

The sleeve 65 includes a central bore 81 which terminates at one end with a short band of right-hand threads 83 and at the other end by a short band of left-hand threads 85.

With further reference to FIGS. 24 and 25 in particular, it is seen that the neck 77 is not threaded over its entire length, but includes a smooth surfaced portion 80 of width equal to the width of the threaded portion 79 thereof. In a further aspect, the outer surface 66 of the sleeve 65 may include a plurality of flats 661 best facilitating gripping by a tool or the fingers of a surgeon to facilitate the rotation of the sleeve 65 and, thereby, movement of the bodies 61, 63 toward or away from one another.

As seen in FIGS. 23–25, the retainers 67, 73 have respective openings designated by the respective reference numerals 87 and 89, as well as respective surfaces 91, 93. The surface 91 tapers from a larger diameter adjacent the wall 95 to a smaller diameter adjacent the wall 96. The surface 93 tapers from a larger diameter adjacent the wall 97 to a smaller diameter adjacent the wall 98. The tapers of the surfaces 91 and 93 is for the same purpose described hereinabove with regard to the other components of the inventive system, to wit, to facilitate insertion in the retainers 61, 63 of the tapered surface 107 of the sleeve 101 of a locking sleeve assembly 100. This is seen with reference to FIGS. 3 and 4, which show two examples of the mounting of a coupler assembly 60 between two rods 10.

As should be understood with particular reference to FIG. 25, when the coupler assembly 60 is assembled together, the body 63, rod 75 is inserted through the sleeve 65 until the threads 79 thereof may be threaded onto the threads 85 of the sleeve 65. Similarly, the body 61 may be mounted on the sleeve 65 by insertion of the rod 69 thereof and threading of the threads 71 thereof onto the threads 83 of the sleeve 65. Threading of the rod 69 into the bore 81 through the use of the threads 83 will cause the rod 69 to be advanced into the bore 81. Similarly, threading of the threads 79 of the neck 77 of the body 63 onto the threads 85 of the sleeve 65 will cause advancement of the rod 75 of the body 63 into the bore 81.

As stated hereinabove, the outer diameter of the rod 75 is smaller than the inner diameter of the bore 70 in the rod 69, so that the rod 75 of the body 63 may slide within the bore 70 of the rod 69 of the body 61 to thereby facilitate the guidance of inward and outward movements of the respective bodies 61, 63 with respect to one another.

In an important aspect, the unthreaded surface 80 of the neck 77 allows the threaded portion 79 of the neck 77 to be threaded past the threaded portion 85 of the bore 81 of the sleeve 65. When this has been accomplished, thereafter, the sleeve 65 may be rotated with respect to the body 63 without reciprocating with respect thereto. Thus, the sleeve 65 may be premounted on the body 63 with the threads 85 and 79 being threaded past one another so that threads 85 of the sleeve 65 are lying in overlying relation over the smooth surface 80 of the neck 77. Thereafter, the sleeve 65 may be rotated with respect to the body 63 in a direction causing advancement of the threaded rod 69 of the body 61 into the bore 81 with the bore 70 of the rod 69 advancing over the relatively stationary rod 75 of the body 63.

In this way, adjustments of the length of the coupler assembly 60, from end to end, may easily be accomplished through rotations of the sleeve 65.

As best seen in FIGS. 3 and 4, the coupler assembly 60 is mounted between two rods 10 with the openings 87, 89 facing either in the same direction or in opposite directions, as desired. As described hereinabove, the surfaces 91, 93 are placed in engagement over the tapered surfaces 107 of sleeves 101 forming a part of respective locking sleeve assemblies 100. Thereafter, lock nuts 103 are threaded over the threaded portion 111 of the sleeves 101 until the flanges 125 thereof bear against the walls 96 or 98 (FIG. 24) of the respective bodies 61, 63. Further threading of the lock nuts 103 on the respective threaded portions 111 of the sleeves 101 will cause pulling of the tapered surfaces 107 of the sleeves 101 into the respective recesses 91, 93 to thereby tighten the bodies 61, 63 in mounted relation over the locking sleeve assemblies 100 and thereby the rods 10. Cut portions 62 in the respective openings 87, 89 are provided to allow the sleeves 101 to be inserted into the recesses 91, 93 without having to move the shoulders 109 of the sleeves 101 completely past the respective walls 95, 98 thereof. Analogous structure to the cut portions 62 shown in FIG. 24 is seen with regard to the reference numeral 222 in FIG. 12 and the reference numeral 182 in FIG. 13 and reference numeral 922 in FIG. 18.

As such, hereinabove, all of the components which form a part of the inventive posterior spinal system have been described in great detail. In light of such description, the examples shown in FIGS. 1 and 7 should be understood to be merely examples of the numerous combinations of components which may be combined together to mount two smooth surfaced rods 10 in predetermined spaced relation with respect to one another on the posterior spine to correct the various deformities and conditions described hereinabove.

With the various components making up the inventive posterior spinal system having been described hereinabove, it is believed to be instructive to describe in detail an example of a method of performing surgery using the posterior spinal system of the present invention.

In installing a mid-line clamp assembly on the posterior spine between two adjacent smooth surfaced rods, pre-operative planning is undertaken wherein the curved magnitude limits of safe correction and levels of fusion are determined according to standard surgical procedures. Mid-line clamps are placed at selected levels throughout the to be fused segment and the necessary number and orientation of each component is determined.

Exposure, decortication and grafting techniques are performed according to standard surgical procedures.

In preparing the site of the surgery, the first spinous process cut is made in the transverse plane at the base of the inferior articular facets. A suitable clamp installer is placed on each level to be instrumented and is used to gauge the second cut to the spinous process. The second cut is parallel to and approximately 0.2 inches posterior to the anterior surface of the lamina. In the preferred mode of operating, all cuts are executed using a Hall micro E sagittal saw. Prior to removal of the clamp installer, the required clamp size is determined therefrom.

Each appropriate sized clamp for implantation is placed on a suitable clamp holder instrument and is thereafter placed on the respective vertebra by sliding the inferior clamp shoe under the inferior lamina and dropping in the superior shoe through the superior lamina notch and cinching into place. The clamp holder is then used to maintain approximation of the clamp halves.

Two smooth surfaced rods 10 of appropriate length to facilitate correction and maintenance of the spine are contoured through the utilization of aluminum templates and rod benders. The appropriate number of locking sleeve assemblies 100, as determined pre-operatively, are placed on the rods 10 pointing in the proper directions for fixation of the mid-line clamps 20 and couplers 60. Hook bodies 140 are placed on suitable hook body holders and are then placed on the mid-line clamp studs leaving the hook body holders in place for manipulation of the hook bodies 140 during correction. For this purpose, the holes 142, best seen in FIG. 22, on the hook bodies 140 are employed.

Lateral correction is achieved by cantilever loading utilizing hook body holders to manipulate the hook bodies 140, with a locking sleeve introducer or surgical slider instrument being used to manipulate the locking sleeves. Both a surgical rod pusher instrument and lateral approximator may be used to provide mechanical advantage as needed. Locking sleeves are placed into the hook bodies 140 and are seated with the locking sleeve introducer instrument, thus maintaining correction.

Locking sleeves are placed in the hook bodies 140, utilizing hook body holders, locking sleeve introducers, rod pushers and sagittal approximators as necessary. The locking sleeves are seated as explained hereinabove, and any additional amounts of distraction or compression are now imposed on the system using rod clamps and a distractor. A suitable locking sleeve cincher instrument is used to fully seat the locking sleeve and the locking nut is finger tightened. Further tightening of the locking sleeves and nuts is achieved through the use of a clamp cincher to provide approximately 80% of required clamping force. Final nut tightening is accomplished through the use of an appropriate wrench.

The system is finally secured through the use of the required number of coupler assemblies 60 which are placed on the rods 10 via locking sleeves assemblies 100 and are tightened onto the rods 10 thereby. The sleeves 65 of the coupler assemblies 60 are rotated in a desired direction to move the bodies 61, 63 either toward or away from one another to provide and maintain the desired separation between the rods 10 and facilitate lamina contact of the bodies to improve stability. In this way, the coupler assemblies act as turnbuckles.

Thereafter, the surgical site is closed using standard surgical techniques The above described surgical process may be followed with reference to FIG. 1 and the associated figures, since FIG. 1 shows examples of mid-line clamps 20 and coupler assemblies 60 as assembled on two smooth surfaced rods 10.

With reference, now, to the example shown in FIG. 7 and associated figures, the technique employed in placing hooks on the posterior spine will be described in detail.

In a first aspect, pre-operative planning is accomplished and hook sites, curve magnitude and levels of fusion are all determined according to standard surgical procedures. The necessary number and orientation of each component is also determined thereby.

Thereafter, exposure of the site is accomplished as per standard surgical techniques.

Thereafter, hook site preparation is performed as per standard Harrington and Cotrel-Dubousset procedures.

Hook placement is performed utilizing hook holders and stabilizers in a manner according to typical Harrington and Cotrel-Dubousset procedures.

Thereafter, two smooth surfaced rods 10 of appropriate length are contoured through the utilization of rod benders and aluminum templates to the desired contour of the spinal column. The appropriate number of locking sleeve assemblies 100 for each rod 10 are placed on each rod 10 in a necessary orientation for each hook and coupler site.

Cantilever correction as well as distraction/compression techniques may now be utilized. Lateral and sagittal approximators as well as rod pushers and distractors are provided to facilitate these correction modes. Cotrel-Dubousset correction techniques may be utilized where necessary. Upon correction at each nodal site, a locking sleeve will be placed into the recess in the open backed body of a hook utilizing the appropriate hook holders and locking sleeve assembly introducer or surgical slider instrument. In the preferred mode of use, lateral correction will precede sagittal correction.

Thereafter, locking sleeves are fully seated, utilizing a locking sleeve cincher instrument and wrench. Coupler assemblies 60 are placed at the appropriate levels and are distracted or compressed where necessary and desired to establish and maintain the desired spacing between the rods 10. Such distraction or compression enhances structural stability.

Thereafter, closure is as per standard surgical techniques.

Of course, where desired in either of the surgical procedures described hereinabove, pedicle screws (not shown) may be employed having studs similar in construction to the studs incorporated in the mid-line clamp assemblies as particularly illustrated with reference numerals 31 and 37 in FIGS. 11 and 15, as well as with reference numerals 271, 277 and 278 in FIG. 14. Thus, such a spinal pedicle screw may be affixed to a respective rod 10 through the use of a hook body 140 as should be understood.

Now, the inventive system and examples of methods of use thereof having been described in detail, further preferred details of the individual components will now be set forth.

The two embodiments of mid-line clamp assembly disclosed herein are worthy of discussion.

The inferior and superior shoes of the mid-line clamp assemblies have been optimized through cadaver testing, which testing determined the load carrying ability of the lamina structure. The studs are positioned on the respective clamp halves so as to ensure hook body contacts with the lamina. The head of each stud is flat to minimize lateral profile. As described hereinabove, the small mid-line clamp assembly includes one stud on each clamp half, whereas the large mid-line clamp assembly includes two studs on the superior clamp half. It has been found that the small clamp may have an inadequate size to permit the placement of three studs thereon. If a clamp larger than the small clamp is used, such as, for example, the large clamps 260 illustrated in FIG. 14, three studs may be included.

Any suitable spinal hook style may be adapted for use with the locking sleeve assemblies of the present invention by inclusion of a tapered recess enabling attachment of the tapered recess of the hook to the tapered sleeve of the locking sleeve assembly as described herein. Three such styles of hooks which have been adapted with open back and tapered recess features of present invention are described above as the bifid hook 180, the lamina hook 220 and the Andre hook 200.

Concerning the bifid style hook 180, best seen in FIGS. 9 and 13, this hook has a fork spacing 188. The forks taper in to provide wedging of the pedicle and two sizes of shoe that may be provided to accommodate for varying lamina heights allowing more posterior placement of the hook shoe while minimizing posterior profile. Excessive notching of the facet and lamina would expose the nerve root and cause the unsafe possibility of striking the nerve root upon insertion.

The lamina hook 220, best seen in FIGS. 10 and 12, is designed to have the same size shoe as an Edwards Anatomic hook (mentioned in the Background), except that shorter shoe height is provided to minimize canal intrusion during insertion.

The shoe of the Andre hook 200, best seen in FIG. 26, may utilize a narrower shoe to allow the placement of two hooks at a single level.

Concerning the locking sleeve assembly 100 and the coupler assembly 60, the radially outwardly extending flange 125 of the lock nut 103 of the locking sleeve assembly 100 is designed to have a sufficient diameter that when the locking sleeve assembly 100 is being used to maintain a coupler assembly 60 in place between two adjacent smooth surfaced rods 10, when the locking nut 103 is appropriately tightened on the sleeve 101, the flange 125 will interfere with the turnbuckle portion 65 termed hereinabove the sleeve of the coupler assembly 60, to thereby prevent loosening of the turn-buckle.

Of course, the components described hereinabove as forming an integral part of the inventive system may be made of any desired materials so long as they exhibit required strength and flexibility as well as being inert and not causing the body to have a rejection reaction. For example, the smooth surfaced rods may be made from cold-worked stainless steel which due to the smooth surface configuration exhibits fatigue and flexibility characteristics superior to rods of much larger diameter which have threaded or knurled surfaces.

As such, a posterior spinal system has been disclosed in terms of smooth surfaced rods, a locking sleeve assembly designed to be used to affix all other system components to the rods and in terms of the system components, including mid-line clamps with hook bodies, hooks, screws with hook bodies, coupler assemblies and any and all other suitable fixation devices.

Of course, various changes, modifications and alterations in the teaching of the present invention may be contemplated by those skilled in the art without departing from the intended spirit and scope of the present invention.

We claim:

1. A spinal locking sleeve assembly and an elongated spinal rod and another structure for use in a spinal implant system, wherein said assembly interconnects the elongated rod with the structure, wherein said structure has a tapered passage therethrough and a sidewall adjacent to a terminus of said passage, said assembly comprising:
   a) an elongated sleeve having a continuous bore therethrough, said sleeve having a first end with a tapered outer surface and a
   b) at least one split in said sleeve extending into at least a portion of each of said first and second ends thereof;
   c) a lock nut having an internal passageway with threads complementary to the threads of said second end;
   d) said bore being sized to slidably receive said rod therethrough;
   e) said tapered outer surface of said sleeve being insertable into said tapered passage of said structure with said rod in said bore, to form an interference fit between the two tapered surfaces, and wherein said passage includes an open back wherein the open back has a width greater than the diameter of said elongated spinal rod.

2. A spinal locking sleeve assembly and an elongated spinal rod and another structure for use in a spinal implant system, wherein said assembly interconnects the elongated rod with the structure, wherein said structure has a tapered passage therethrough and a sidewall adjacent to a terminus of said passage, said assembly comprising:
   a) an elongated sleeve having a continuous bore therethrough, said sleeve having a first end with a tapered outer surface and a second threaded end;
   b) at least one split in said sleeve extending into at least a portion of each of said first and second ends thereof;
   c) a lock nut having an internal passageway with threads complementary to the threads of said second end;
   d) said bore being sized to slidably receive said rod therethrough;
   e) said tapered outer surface of said sleeve being insertable into said tapered passage of said structure with said rod in said bore, to form an interference fit between the two tapered surfaces, and wherein said lock nut is threaded onto said second end of said sleeve until said lock nut engages said sidewall, and wherein further rotation of the lock nut causes said at least one split to narrow to cause said sleeve to frictionally grip said rod, to interconnect said rod and structure.

3. The invention of claim 2, wherein said passage is tapered in the same direction as the taper of said tapered outer surface as placed in said passage.

4. The invention of claim 2, wherein said lock nut includes a radially outwardly extending flange adapted to engage said sidewall of said structure.

5. The invention of claim 2, wherein said at least one split comprises a plurality of circumferentially-spaced splits, one of said splits extending the entire longitudinal extent of said sleeve.

6. The invention of claim 5, wherein said sleeve has a longitudinal axis, said splits being at an oblique angle to said axis.

7. The invention of claim 2, further including a shoulder separating said first and second ends of said sleeve.

8. The invention of claim 2, wherein said passage is open backed.

9. The invention of claim 2, wherein said structure comprises a hook body.

10. The invention of claim 2, wherein said structure comprises a coupler assembly.

11. The invention of claim 1, wherein said structure comprises a hook having an extending hook shoe.

12. The invention of claim 8, wherein said structure comprises a hook body.

13. The invention of claim 8, wherein said structure comprises a coupler assembly.

14. The invention of claim 8, wherein said structure comprises a hook.

15. A spinal locking sleeve assembly and an elongated spinal rod and another structure for use in a spinal implant system, wherein said assembly interconnects the elongated rod with the structure, wherein said structure has a tapered passage therethrough and a sidewall adjacent to a terminus of said passage, said assembly comprising:
   a) an elongated sleeve having a continuous bore therethrough, said sleeve having a first end with a tapered outer surface and a second end with a securing means thereon;
   b) at least one split extending into said sleeve;
   c) a lock means having an internal passageway with a mating securing means complementary to the securing means on the sleeve;
   d) said bore being sized to slidably receive said rod therethrough;
   e) said tapered outer surface of said sleeve being insertable into said tapered passage of said structure with said rod in said bore, to form an interference fit between the two tapered surfaces, and wherein said passage includes an open back wherein the open back has a width greater than the diameter of said elongated spinal rod.

16. A spinal locking sleeve assembly and an elongated spinal rod and another structure for use in a spinal implant system, wherein said assembly interconnects the elongated rod with the structure, wherein said structure has a tapered passage therethrough and a sidewall adjacent to a terminus of said passage, said assembly comprising:
a) an elongated sleeve having a continuous bore therethrough, said sleeve having a first end with a tapered outer surface and a second end with a securing means thereon;
b) at least one split extending into said sleeve;
c) a lock means having an internal passageway with a mating securing means complementary to the securing means on the sleeve;
d) said bore being sized to slidably receive said rod therethrough;
e) said tapered outer surface of said sleeve being insertable into said tapered passage of said structure with said rod in said bore, to form an interference fit between the two tapered surfaces, and wherein said lock means is secured onto the second end of said sleeve so that said lock means engages said sidewall, and wherein this securement of the lock means causes said at least one split in the sleeve to narrow to cause the sleeve to frictionally grip said rod, to interconnect said rod and structure.

17. The invention of claim 15, wherein said passage is tapered in the same direction as the taper of said tapered outer surface as placed in said passage.

18. The invention of claim 16, wherein said lock means includes a radially outwardly extending flange adapted to engage said sidewall of said structure.

19. The invention of claim 15, wherein said at least one split comprises a plurality of circumferentially-spaced splits, one of said splits extending the entire longitudinal extent of said sleeve.

20. The invention of claim 19, wherein said sleeve has a longitudinal axis, said splits being at an oblique angle to said axis.

21. The invention of claim 16, further including a shoulder separating said first and second ends of said sleeve.

22. The invention of claim 16, wherein said passage is open backed.

23. The invention of claim 15, wherein the securing means on the sleeve and the mating securing means on the lock means are mating threads.

24. A spinal locking sleeve assembly and an elongated spinal rod and another structure for use in a spinal implant system, wherein said assembly interconnects the elongated rod with the structure, wherein said structure has a tapered passage therethrough and a sidewall adjacent to a terminus of said passage, said assembly comprising:
a) an elongated sleeve having a continuous bore therethrough, said sleeve having a first end with a tapered outer surface and a second threaded end;
b) at least one split in said sleeve extending into at least a portion of each of said first and second ends thereof;
c) a lock nut having an internal passageway with threads complementary to the threads of said second ends;
d) said bore being sized to slidably receive said rod therethrough;
e) said tapered outer surface of said sleeve being insertable into said tapered passage of said structure with said rod in said bore, to form an interference fit between the two tapered surfaces, and wherein said lock nut has an end face, and wherein the lock nut is threaded onto said second end of said sleeve, and wherein said lock nut is axially movable relative to the structure along said second end of said sleeve until said end face of the lock nut engages said sidewall, and wherein further rotation of the lock nut causes said at least one split to narrow to cause said sleeve to frictionally grip said rod, to interconnect said rod and structure.

25. A spinal locking sleeve assembly and an elongated spinal rod and another structure for use in a spinal implant system, wherein said assembly interconnects the elongated rod with the structure, wherein said structure has a tapered passage therethrough and a sidewall adjacent to a terminus of said passage, said assembly comprising:
a) an elongated sleeve having a continuous bore therethrough, said sleeve having a first end with a tapered outer surface and a second end with a securing means thereon;
b) at least one split extending into said sleeve;
c) a lock means having an internal passageway with a mating securing means complementary to the securing means on the sleeve;
d) said bore being sized to slidably receive said rod therethrough;
e) said tapered outer surface of said sleeve being insertable into said tapered passage of said structure with said rod in said bore, to form an interference fit between the two tapered surfaces, and wherein said lock means has an end face, and wherein the lock means is securable onto said second end of said sleeve, and wherein said lock means is axially movable relative to the structure along the second end of said sleeve until said end face of said lock means engages said sidewall, and wherein further advancement of the lock means causes said at least one split in the sleeve to narrow to cause the sleeve to frictionally grip said rod, to interconnect said rod and structure.

* * * * *